United States Patent [19]

Issei et al.

[11] 4,294,665
[45] Oct. 13, 1981

[54] SEPARATION OF ACETONITRILE FROM CRUDE OLEFINICALLY UNSATURATED NITRILE

[75] Inventors: Katsuta Issei; Tanaka Tetsuo, both of Kurashiki, Japan

[73] Assignee: Asahi Kasei Kogyo Kabushiki Kaisha, Osaka, Japan

[21] Appl. No.: 115,865

[22] Filed: Jan. 28, 1980

[30] Foreign Application Priority Data

Feb. 2, 1979 [JP] Japan ............................ 54/11109

[51] Int. Cl.³ ............... B01D 3/00; C07C 121/32
[52] U.S. Cl. ........................... 203/50; 203/81; 203/84; 203/DIG. 3; 203/DIG. 19; 260/465.3; 260/465.9
[58] Field of Search ............ 203/91, 94, 96, DIG. 3, 203/DIG. 19, 39, 71, 73–75, 77, 78, 80–82, 84, 50; 260/465.9, 465.3

[56] References Cited

U.S. PATENT DOCUMENTS

| | | | |
|---|---|---|---|
| 3,201,918 | 8/1965 | Sennewald et al. | 260/465.9 |
| 3,352,764 | 11/1967 | Tyler | 203/DIG. 19 |
| 3,445,347 | 5/1969 | Borrel et al. | 203/DIG. 19 |
| 3,507,755 | 4/1970 | Bitners et al. | 260/465.3 |

*Primary Examiner*—Frank Sever
*Attorney, Agent, or Firm*—Sprung, Felfe, Horn, Lynch & Kramer

[57] ABSTRACT

A process for separating acetonitrile from a crude olefinically unsaturated nitrile which comprises passing a reaction gas obtained in the ammoxidation of propylene or isobutylene through a quenching column, an absorption column with water, an extractive distillation column for the olefinically unsaturated nitrile and a stripping column for acetonitrile successively, condensing the acetonitrile-containing vapor from the top of the stripping column, evaporating the condensate acetonitrile-containing liquid into a gas, subjecting the resulting gas mixture to a vapor-liquid separation and subjecting the gas separated to an incineration while withdrawing the liquid separated.

11 Claims, 1 Drawing Figure

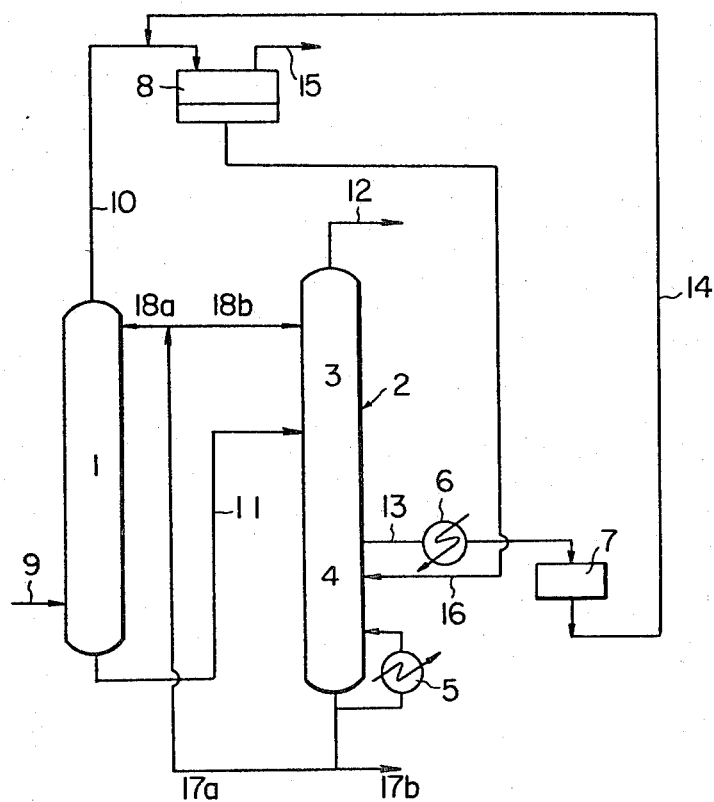
FIGURE

SEPARATION OF ACETONITRILE FROM CRUDE OLEFINICALLY UNSATURATED NITRILE

BACKGROUND OF THE INVENTION

1. Field of the Invention

The present invention relates to a process for separating acetonitrile as the by-product in a crude olefinically unsaturated nitrile such as acrylonitrile and methacrylonitrile produced in the ammoxidation of propylene or isobutylene. More particularly, it relates to a process for efficiently using acetonitrile separated as a fuel or incinerating the acetonitrile without deteriorating the quality of the olefinically unsaturated nitrile.

2. Description of the Prior Art

The reaction gas obtained in the ammoxidation of propylene or isobutylene is fed to a quenching column where unreacted ammonia is removed. Then the reaction gas quenched is counter-currently contacted with absorbing water in an absorption column, and a reaction waste gas containing unreacted propylene or unreacted isobutylene, carbon monoxide, carbon dioxide, nitrogen, etc. is discharged from the top of the absorption column while an aqueous solution containing acrylonitrile or methacrylonitrile, acetonitrile, hydrogen cyanide and other impurities is withdrawn from the bottom of the absorption column. The aqueous solution thus obtained is fed to an extractive distillation column, to the upper part of which water is introduced as an extractant. From the top of the extractive distillation column are recovered acrylonitrile or methacrylonitrile, hydrogen cyanide and a small amount of water while an aqueous solution mainly containing acetonitrile is withdrawn from the bottom of the extractive distillation column. The aqueous acetonitrile-containing solution is introduced to a stripping column and from the bottom of the stripping column is recovered water substantially not containing acetonitrile and recycled to the absorption column and the extractive distillation column as the absorbing water and the extractant, respectively. As a result, acetonitrile, low boiling point impurities such as acetone, acrolein, oxazole, propionitrile and a small amount of hydrogen cyanide, and a small amount of water are withdrawn from the top of the stripping column. The aqueous solution containing acetonitrile withdrawn from the top of the stripping column is usually employed as a fuel or subjected to incineration. In this case, the concentration of acetonitrile in the aqueous acetonitrile-containing solution is usually as low as about 2% by weight and in order to impart natural combustibility to the aqueous solution, the concentration of the acetonitrile in the aqueous solution is required to be at least about 10% by weight. Accordingly, the stripping column requires a device for enriching acetonitrile, and for this purpose is generally employed a distillation column equipped with a reflux condenser. Such a device, however, increases the operational cost and in addition, the amount of heat for evaporation water in the aqueous solution and heating the evaporated water employed in incineration, i.e. the amount of an auxiliary fuel required is increased. According to Japanese Patent Publication No. 36892/1970, part of the bottoms liquid in the extractive distillation column is recycled as the absorbing water to the upper part of the absorption column and is contacted with a waste gas in the absorption column, whereby the acetonitrile in the bottoms liquid of the extractive distillation column is evaporated into the waste gas in the absorption column and then the resulting waste gas from the absorption column is subjected to incineration. In this method vapor-liquid contact is conducted by contacting an aqueous solution of a low concentration, i.e. about 2,500 ppm of acetonitrile from the bottom of the extractive distillation column with the waste gas in the absorption column. It is preferred that the temperature of water flowing down in the absorption column is low in order for the water to absorb the reaction exhaust gas therein. However, when the temperature is low, the evaporation of acetonitrile and other low boiling impurities into the waste gas in the absorption column is insufficient. As a result, the concentrations of acetonitrile and other low boiling impurities in the aqueous solution which is fed to the extractive distillation column from the bottom of the absorption column are increased, that is, acetonitrile and other low boiling impurities are recycled from the bottom of the extractive distillation column to the upper part of the absorption column and the extractive distillation column. Thus, the separation of acetonitrile and other low boiling impurities must be conducted under more severe conditions and the concentrations of acetonitrile and other low boiling impurities in the crude olefinically unsaturated nitrile from the top of the extractive distillation column are disadvantageously increased. Further, according to this conventional process, substantially the entire amount of acetonitrile and other low boiling impurities produced in the ammoxidation of propylene or isobutylene cannot be withdrawn from the waste gas from the absorption column and as a result, the remaining acetonitrile is withdrawn from the top of the stripping column and subjected to incineration. Thus, the enriching device for acetonitrile provided in the stripping column is still necessary, the operational cost cannot be completely reduced and the auxiliary fuel used in an incinerator is still required. According to Japanese Patent Application No. 149,620/1975, a waste gas having a little higher temperature from the top of the absorption column is blown from the bottom of a stripping column succeeding to an extractive distillation column to conduct stripping of acetonitrile in an aqueous solution from the bottom of the extractive distillation column, and the gas discharged from the top of the stripping column is incinerated. Also, in this process an aqueous solution of a low concentration, i.e. about 2,300 ppm of acetonitrile from the bottom of the extractive distillation column is contacted with a waste gas from the absorption column in a plate column. Furthermore, the waste gas for incineration from the absorption column contains about 10% by volume to about 30% volume of water and the amount of an auxiliary fuel employed for incineration of acetonitrile as a fuel is disadvantageously increased.

SUMMARY OF THE INVENTION

According to this invention there is provided a process for separating acetonitrile from a crude olefinically unsaturated nitrile which comprises passing a reaction gas obtained in the ammoxidation of propylene or isobutylene through a quenching column, an absorption column with water, an extractive distillation column for the olefinically unsaturated nitrile and a stripping column for acetonitrile successively, condensing the acetonitrile-containing vapor from the top of the stripping column, evaporating the condensate acetonitrile-containing liquid into a gas, subjecting the resulting gas mixture to a vapor-liquid separation and subjecting the gas separated to an incineration while withdrawing the liquid separated.

BRIEF DESCRIPTION OF THE DRAWINGS

FIGURE shows a flow diagram of a typical embodiment of the process according to this invention.

DETAILED DESCRIPTION OF THE INVENTION

The gases which can employed for evaporating the condensate acetonitrile-containing liquid therein in this process include the waste gas discharged from the top of the absorption column and the air for combustion in an incinerator. Of these gases, the waste gas from the top of the absorption column is preferred since the waste gas as such must be subjected to incineration and it is the gas discharged from a series of purification equipment. Furthermore, when the condensate acetonitrile-containing liquid usually having a concentration of acetonitrile of about 2% by weight from the top of the stripping column is evaporated into the waste gas from the absorption column without refluxing and then the remaining liquid after removal of acetonitrile and traces of other low boiling impurities is returned to the lower part of the extractive distillation column, the concentration of acetonitrile in the remaining liquid stripped of acetonitrile is reduced to about 1% by weight while the concentration of acetonitrile in the condensate acetonitrile-containing liquid is increased to about 3% by weight and as a result, the concentration of acetonitrile reaches equilibrium without disturbing the process. That is, a continuous recycling operation is possible without affecting the quality of acrylonitrile from the top of the extractive distillation column. In this case, the stripping column does not require a device for enriching acetonitrile such as a distillation column equipped with a reflux condenser. Accordingly, the operational cost of such a device and its operational troubles such as clogging of concentrated hydrogen cyanide can be eliminated. The acetonitrile-containing vapor from the top of the stripping column contains, in addition, other low boiling impurities such as acetone, acrolein, oxazole, propionitrile and a small amount of hydrogen cyanide and substantially the entire amount of these impurities produced in the ammoxidation can be evaporated and diffused in a gas. It is preferred that the aqueous acetonitrile-containing liquid has a temperature which is sufficient to evaporate acetonitrile into a gas but which does not evaporate water, that is, a temperature which is lower than the gas from the absorption column or the air for combustion in an incinerator from the viewpoint of minimization of the incinerator and reduction of the auxiliary fuel.

According to the process of this invention, it can be avoided that acetonitrile and other low boiling impurities mix into the crude acrylonitrile or the crude methacrylonitrile at the top of the extractive distillation column. On the other hand, according to the process described in Japanese Patent Publication No. 36892/1970, part of the bottoms liquid of the extractive distillation column is recycled to the upper part of the absorption column and accordingly, mixing of acetonitrile and other low boiling point impurities into the crude acrylonitrile or the crude methacrylonitrile at the top of the extractive distillation column cannot be avoided due to the increase in the concentration of the acetonitrile and other low boiling point impurities in the aqueous solution which is fed to the extractive distillation column from the bottom of the absorption column.

The concentration of acetonitrile in the aqueous acetonitrile-containing liquid which is evaporated and diffused into a gas typically ranges from about 2% by weight to about 80% by weight and preferably from about 3% by weight to about 10% by weight. The amount of the aqueous acetonitrile-containing liquid which can be employed in this process typically ranges from about 0.05 metric ton to about 1.5 metric tons and preferably from about 0.1 metric ton to about 1.0 metric ton per metric ton of acrylonitrile or methacrylonitrile. Any vapor-liquid contacting device such as a spray column, a packed column can be employed as a device for evaporating and diffusing the aqueous acetonitrile-containing liquid into a gas. In this process, a spray column is preferred due to its simpleness and low cost for operation.

As the vapor-liquid separator, a cyclone can be employed but a simple gravity sedimentation device is enough.

Any conventional incinerator such as a forced draft furnace, natural draft furnace can be employed.

In the process of this invention, the liquid after the vapor-liquid separation can be recycled either to the bottom of the extractive distillation column, to the stripping column or to the bottom of the quenching column.

When the liquid after the vapor-liquid separation is returned to the bottom of the quenching column, acetonitrile and other low boiling impurities are stripped in the quenching column and as a result, it might be feared that the acetonitrile and impurities stripped increase the load of the subsequent absorption column and extractive distillation column. However, the concentration of acetonitrile in the remaining liquid stripped of acetonitrile in the waste gas from the absorption column is as low as about 1% by weight and also the amount of the remaining liquid is small. Further, part of the acetonitrile and impurities is withdrawn from the bottom of the quenching column. Thus, the recycling operation can be conducted without disadvantageously affecting the quality of the acrylonitrile at the top of the extractive distillation column.

In this invention it is preferred from the viewpoint of energy saving that one rectifying column having an extractive distillation section at its upper part and a stripping section at its lower part is employed for the above described extractive distillation column and stripping column. The rectifying column of this type is described in Japanese Patent Publication No. 6134/1978.

In this case, when the condensate liquid of an acetonitrile-containing vapor from the upper part of the stripping section which contains about 10% by weight of acetonitrile is evaporated into the waste gas in the absorption column without refluxing to separate acetonitrile and a small amount of low boiling point impurities and the remaining liquid is returned either to the lower part of the extractive distillation section or the stripping section or to the bottom of the quenching column, the concentration of acetonitrile in the remaining liquid stripped of acetonitrile is reduced to about 1% by weight and the process can be continuously conducted without any disturbance. It is also possible that the concentration of acetonitrile is increased by refluxing.

This invention will now be explained in more detail with reference to the accompanying drawing which is in the form of a flow diagram showing one embodiment of the process according to this invention in which one rectifying column having an extractive distillation section and a stripping section is employed for the extractive distillation column and stripping column.

In FIGURE, numeral 1 represents an absorption column; numeral 2 a rectifying column; numeral 3 the extractive distillation section of the rectifying column; numeral 4 the stripping section of the rectifying column; numeral 5 a reboiler, numeral 6 a condenser; numeral 7 a drum; and numeral 8 a vapor-liquid separator.

A reaction gas in the ammoxidation of propylene or isobutylene is fed through line 9 to the lower part of absorption column 1 and contacted with absorbing water fed to the upper part of absorption column 1, and from the top of absorption column 1 is discharged a waste gas having a temperature of about 40° C. On the other hand, the absorbed solution is withdrawn from the bottom of absorption column 1 and fed through line 11 to extractive distillation section 3 in rectifying column 2. The liquid in rectifying column 2 is heated by steam at reboiler 5. From the top of extractive distillation section 3 is withdrawn through line 12 a crude acrylonitrile containing acrylonitrile, hydrogen cyanide and water. From the upper part of stripping section 4 is withdrawn through line 13 a vapor containing acetonitrile and condensed by cooling in condenser 6 and stored in drum 7. Then the liquid stored in drum 7 is sprayed in the form of liquid through line 14 into line 10 for the waste gas from absorption column 1. The acetonitrile and other low boiling impurities sprayed in the form of liquid is evaporated and diffused into the waste gas from absorption column 1 and fed to vapor-liquid separator 8. The gas containing substantially the entire amount of acetonitrile and other low boiling impurities formed in the ammoxidation of propylene or isobutylene can be separated from liquid in vapor-liquid separator 8 and fed through line 15 to an incinerator. On the other hand, the liquid separated in vapor-liquid separator 8 is recycled through line 16 to stripping section 4 of rectifying column 2. From the bottom of stripping section 4 of rectifying column 2 is withdrawn water substantially not containing acetonitrile, and part of the water is discharged through line 17b as a waste while the remaining water is recycled to the upper part of absorption column 1 through line 18a and to the upper part of extractive distillation section 3 of rectifying column 2 through line 18b.

The following Examples are given to illustrate the present invention more specifically. However, it should be understood that the invention is in no way limited by these Examples. All parts and percentages in these Examples are by weight unless otherwise indicated.

EXAMPLE

Separation of Acetonitrile from Aqueous Acetonitrile-containing Solution Separated from Crude Acrylonitrile At the 25th plate from the bottom of a rectifying column having an extractive distillation section and a stripping section and 85 plates was withdrawn a vapor at a rate of 0.2 metric ton per ton of acrylonitrile and condensed to about 40° C. in a condenser and then stored in a drum. The vapor contained 8.36% of acetonitrile, 3.09% of hydrogen cyanide, 87.0% of water and a small amount of other low boiling impurities including acetone, acrolein, oxazole, propionitrile, etc. The condensate liquid stored in the drum was sprayed at a rate of 0.2 metric ton per ton of acrylonitrile into a waste gas having a temperature of about 40° C. and a flow rate of $4.06 \times 10^3$ Nm$^3$ per metric ton of acrylonitrile which had been discharged from the top of an absorption column to evaporate most of the organic compounds therein. The remaining liquid containing 1.22% of acetonitrile, 1.29% of hydrogen cyanide, 97.0% of water and traces of other low boiling impurities was withdrawn from the vapor-liquid separator at a flow rate of 0.19 metric ton per ton of acrylonitrile. On the other hand, the water content of the waste gas withdrawn from the vapor-liquid separator was as low as about 6.5 to about 7.0% by volume and the waste gas contained substantially the entire amount of acetonitrile and other low boiling impurities formed in the ammoxidation of propylene and had a flow rate of $4.07 \times 10^3$ Nm$^3$ per metric ton of acrylonitrile. In this operation, any increase of low boiling impurities such as acetonitrile, hydrogen cyanide, acetone, oxazole, acrolein and propionitrile in the acrylonitrile product could not be observed.

COMPARATIVE EXAMPLE

At the 25th plate from the bottom of the same rectifying column as in Example was withdrawn a vapor at a rate of 0.45 metric ton per ton of acrylonitrile and introduced to the bottom of an enriching column for acetonitrile having 10 plates and from the top of the enriching column was obtained a distillate containing 21.6% of acetonitrile, 5.0% of hydrogen cyanide, 73.4% of water and traces of impurities at a rate of 0.09 metric ton per metric ton of acrylonitrile. This distillate was sprayed and incinerated in an incinerator. This process required 0.23 metric ton of steam in the rectifying column per metric ton of acrylonitrile more than the process of Example and the amount of an auxiliary fuel employed in the incinerator was remarkably increased.

What is claimed is:

1. A process for separating acetonitrile from a crude olefinically unsaturated nitrile which comprises passing a reaction gas obtained in the ammoxidation of propylene or isobutylene through a quenching column, an absorption column with water, an extractive distillation column for the olefinically unsaturated nitrile and a stripping column for acetonitrile successively, condensing the acetonitrile-containing vapor from the top of the stripping column, evaporating the condensed acetonitrile-containing liquid into the waste gas discharged from the top of the absorption column, subjecting the waste gas containing a gas and a liquid obtained by the evaporation to a vapor-liquid separation subjecting the gas separated thereby to incineration and recycling the liquid thereby separated to a preselected point selected from the group consisting of the bottom of the quenching column, the stripping column and the bottom of the extractive distillation column.

2. The process of claim 1, wherein the liquid after the vapor-liquid separation is recycled to the stripping column.

3. The process of claim 1, wherein the liquid after the vapor-liquid separation is recycled to the bottom of the extractive distillation column.

4. The process of claim 1, wherein the liquid after the vapor-liquid separation is recycled to the bottom of the quenching column.

5. The process of claim 1, wherein the concentration of acetonitrile in the condensed liquid of the acetonitrile-containing vapor is about 2% by weight to about 80% by weight.

6. The process of claim 1, wherein the reaction gas is the one obtained in the ammoxidation of propylene.

7. The process of claim 1, wherein one rectifying column having an extractive distillation section and a stripping section is employed instead of the extractive column and the stripping column and heat is provided to the bottom of the stripping section.

8. The process of claim 7, wherein the liquid after the vapor-liquid separation is recycled to the stripping section of the rectifying column.

9. The process of claim 7, wherein the liquid after the vapor-liquid separation is recycled to the lower part of the extractive distillation section.

10. The process of claim 7, wherein the liquid after the vapor-liquid separation is recycled to the bottom of the quenching column.

11. The process of claim 1, wherein the acetonitrile-containing vapor includes a small amount of acetone, acrolein, oxazole and propionitrile, and substantially the entire amount of these low boiling impurities are evaporated by the evaporation.

* * * * *